United States Patent

Hierlemann et al.

(10) Patent No.: US 6,706,058 B2
(45) Date of Patent: Mar. 16, 2004

(54) RESORBABLE, SYNTHETIC, MEDICAL COATING MATERIAL, METHOD FOR ITS MANUFACTURE AND ITS USE IN MEDICINE

(75) Inventors: Helmut Hierlemann, Goeppingen (DE); Heinrich Planck, Nuertingen (DE)

(73) Assignee: Deutsche Institute fur Textil- und Faserforschung Stuttgart Stiftung des offentlichen Rechts, Denkendorf (DE)

( * ) Notice: Subject to any disclaimer, the term of this patent is extended or adjusted under 35 U.S.C. 154(b) by 367 days.

(21) Appl. No.: 09/930,177

(22) Filed: Aug. 16, 2001

(65) Prior Publication Data

US 2002/0028231 A1 Mar. 7, 2002

(30) Foreign Application Priority Data

Aug. 24, 2000 (DE) .......................................... 100 41 684

(51) Int. Cl.$^7$ .......................... A61L 17/00; A61B 17/04; C08G 63/08
(52) U.S. Cl. ......................... 606/230; 528/354; 528/359
(58) Field of Search ............................... 528/354, 359; 606/230

(56) References Cited

U.S. PATENT DOCUMENTS

| | | |
|---|---|---|
| 5,475,063 A | 12/1995 | Kaplan et al. |
| 5,713,920 A | 2/1998 | Bezwada et al. |

FOREIGN PATENT DOCUMENTS

| | | |
|---|---|---|
| DE | 41 12 489 C2 | 10/1992 |
| DE | 42 29 924 C2 | 3/1994 |
| DE | 43 34 272 C2 | 4/1995 |
| DE | 196 41 334 A1 | 4/1998 |
| DE | 197 06 621 A1 | 8/1998 |
| DE | 197 18 430 A1 | 1/1999 |
| DE | 198 28 416 A1 | 6/1999 |
| EP | 0 401 844 A2 | 12/1990 |
| EP | 0 460 439 A2 | 12/1991 |
| EP | 600 237 A1 | 6/1994 |
| EP | 0 610 731 A1 | 8/1994 |
| EP | 628 587 A2 | 12/1994 |
| EP | 0 707 044 A2 | 4/1996 |
| EP | 0 747 072 | 12/1996 |
| EP | 0 748 634 A2 | 12/1996 |
| EP | 0 835 894 | 4/1998 |
| EP | 0 860 171 | 8/1998 |
| EP | 0 908 482 A1 | 4/1999 |
| WO | WO 94/11441 | 5/1994 |
| WO | WO 98/00065 | 1/1998 |
| WO | WO 99/02168 | 1/1999 |

*Primary Examiner*—Weilun Lo
*Assistant Examiner*—Linh Truong
(74) *Attorney, Agent, or Firm*—Nath & Associates PLLC; Gary M. Nath; Marvin C. Berkowitz

(57) ABSTRACT

The invention relates to a coating material for medical treatment, particularly a wound contact material, of resorbable, synthetic material, which is formed from a terpolymer based on lactide, trimethylene carbonate and ε-caprolactone with a maximum lactide content of 85 wt. %, trimethylene carbonate in the range 5 to 20 wt. % and ε-caprolactone in the range 5 to 20 wt. %, a method for its manufacture and its use.

36 Claims, 1 Drawing Sheet

RESORBABLE, SYNTHETIC, MEDICAL COATING MATERIAL, METHOD FOR ITS MANUFACTURE AND ITS USE IN MEDICINE

DESCRIPTION

1. Field of the Invention

The present invention relates to coating material for medical treatment, particularly wound contact material formed from a resorbable, synthetic material.

2. Background of the Invention

In medical treatment the problem frequently arises of shielding body tissues against undesired influences. This e.g. comprises covering the skin to protect against external effects or in the case of wounds, such as injuries, closure of wounds during surgery, medical implants and the separation of body tissue in adhesion prophylaxis in order to avoid undesired cicatrization and scarring.

For this purpose biocompatible materials based on natural and synthetic substances have been developed. Products are known from non-resorbable materials such as silicone, R, PP, PET, PA and PTFE, as well as partly or completely resorbable products based on collagen, hyaluronic acid, polysaccharides, cellulose and their derivatives, lactic acid or glycolic acid.

Disadvantages arise in the known materials due to their incomplete or very slow decomposition behaviour in the body of the patient. Additionally there is undesired adhesion to body tissue, which leads to bandage changing problems in the case of uses on the skin. This leads to the patient having a prolonged recovery period, associated with personal unpleasant features such as pain and mobility restrictions.

The problem of the invention is to make available a biocompatible coating material of resorbable, synthetic polymer, which overcomes the prior art problems, has a good decomposition and resorption behaviour in vivo combined with good physical and mechanical characteristics, which is easy and inexpensive to manufacture and which can be simply and reliably medically used.

SUMMARY OF THE INVENTION

This problem is solved by a coating material for medical treatment, particularly a wound contact material, of resorbable, synthetic material, characterized in that it is formed from a terpolymer based on lactide, trimethylene carbonate and ε-caprolactone with a lactide content of maximum 85 wt. %, particularly maximum 80 wt. %, trimethylene carbonate in the range 5 to 20 wt. %, particularly 10 to 20 wt. %, and ε-caprolactone in the range 5 to 20 wt. %, particularly 5 to 15 wt. %.

DETAILED DESCRIPTION

Figure 1:
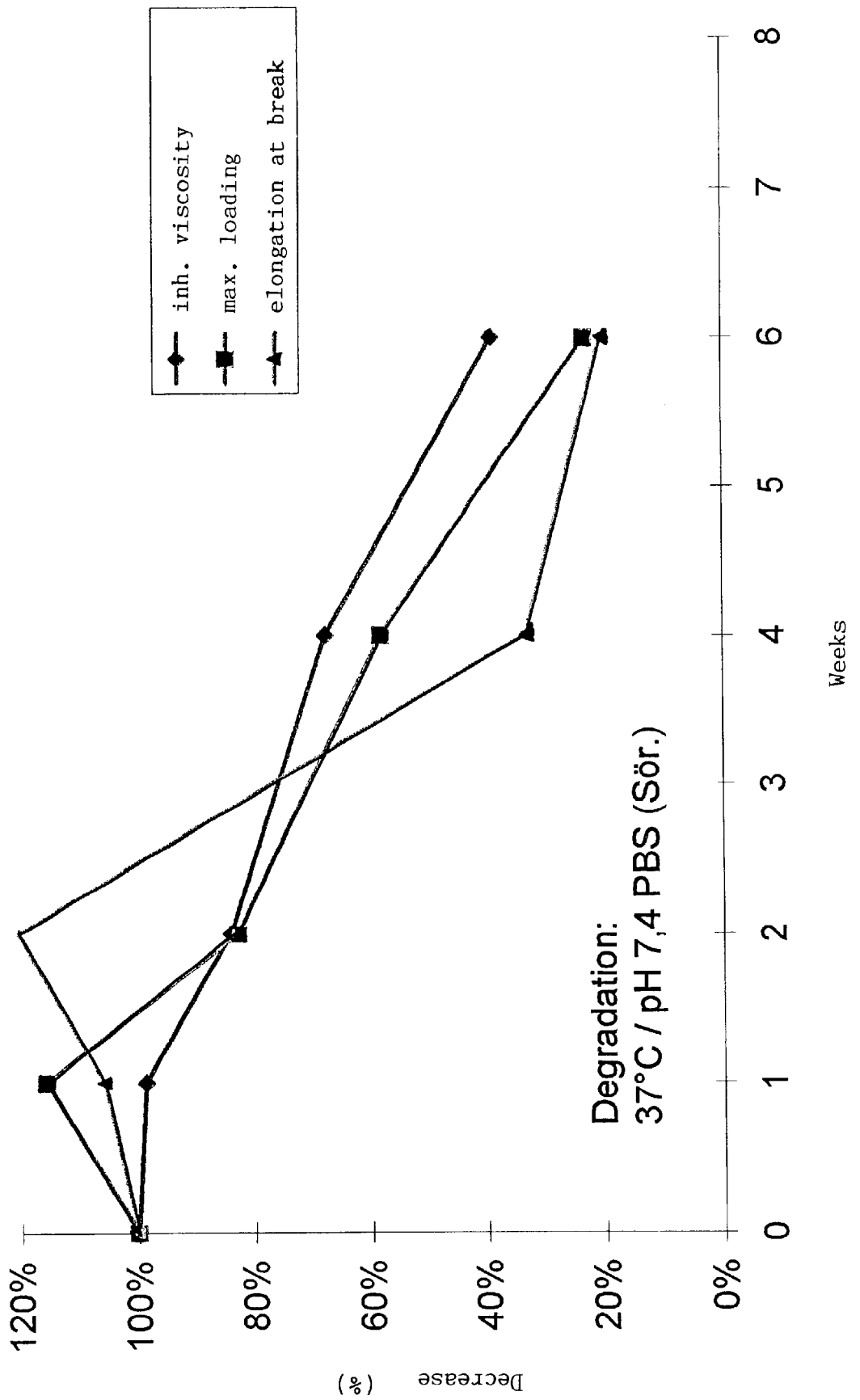
FIG. 1 plots how the degradation of the terpolymer over time modifies its physical and mechanical characteristics.

In a preferred embodiment the terpolymer according to the invention can be formed with a random distribution of the monomers. In another embodiment the terpolymer according to the invention can be in the form of a block polymer of the monomers.

In a preferred embodiment the terpolymer can contain the monomers lactide/trimethylene carbonate/ε-lactone with weight percentage ratios of 85:10:5 to 70:20:10. The lower lactide limit is 65 wt. %. The terpolymer according to the present invention can contain a total of monomers of up to 10 wt. % including the monomers lactide trimethylene carbonate and ε-caprolactone. Preferably the monomer content is between 1 and 9 wt. %.

As lactide components L-lactide, DL-lactide and/or meso-lactide can be used in the terpolymer. With particular preference the lactide component is DL-lactide.

The coating material according to the invention can be characterized in that it has a glass transition point in the temperature range 20 to 40° C., particularly 28 to 37° C. This leads to particular advantages for the use of the material in the patient, whose body temperature is in this range.

The terpolymer can initially have a molecular weight in the range 80,000 to 400,000 Dalton, particularly 90,000 to 250,000 Dalton. Following any gamma radiation treatment, e.g. of 25 kGy such as is used for sterilization purposes, the terpolymer can have a molecular weight range of 50,000 to 150,000 Dalton, particularly 60,000 to 90,000 Dalton. The gamma radiation treatment of the material according to the invention is explained in greater detail hereinafter.

The terpolymer can initially have an inherent viscosity of 0.8 to 2.5 dl/g, particularly 1.0 to 2.0 dl/g. Following any gamma radiation treatment in the sterilized state the terpolymer can have an inherent viscosity of 0.7 to 1.2 dl/g, particularly 0.7 to 1.0 dl/g.

The material according to the invention is more particularly characterized by advantageous mechanical characteristics and good handling. The material can have an elongation of at least 50% at 37° C. At body temperature its modulus can be less than 1,000 N/mm$^2$. At 37° C. its elongation at break can be 50 to 400%, particularly 100 to 300%. The tensile strength of the material according to the invention can be less than 30 N/mm$^2$.

In the case of temperatures in the room temperature range and below the material according to the invention is easy to handle, flexible and extensible. In this way it can be prepared for medical application, e.g. cut to a desired size and applied or used on the patient. Following contact with the patient's body the material becomes increasingly warm and finally reaches the body temperature of the patient. The material according to the invention becomes increasingly plastically deformable, softer, more flexible and extensible until it has almost reached a flowable state. This permits an optimum adaptation to the body area of the patient to be treated.

With temperatures in the range of the human body temperature of 37° C. the extensibility of the material can be up to 250%. Preferably its extensibility at 37° C. is 100%. The increasing flexibilization of the polymer material is also positively influenced by water absorption.

The material according to the invention can be advantageously characterized by water vapour permeability. With pressureless water passage its water vapour permeability can be 20 to 100 ml/m$^2$/h, particularly 40 to 80 ml/m$^2$/h. Thus, it is possible to avoid both a liquid build-up and a drying out in the wound area. A medical product produced according to the invention can physiologically interact with the treated body area of the patient. Metabolic activity in the treated body area is also possible. This stimulates wound healing processes and assists local defence mechanisms. The coating material according to the invention can be advantageously characterized by a barrier function against microorganisms. This prevents an infection, which is always favourable for healing purposes. With topical application a temperature regulation of the wound area is also possible, which also favours healing.

In particularly advantageous manner the terpolymer according to the invention can be characterized in that it is completely resorbable in the body of a patient. This is favourable for good body compatibility when used in humans and animals. The decomposition of the polymer according to the invention takes place in the body of the human or animal by metabolic processes. Body and tissue fluids participate in this process. By hydrolysis the polymer chain is split up into smaller and readily soluble fragments. The fragments are further decomposed, optionally accompanied by the participation of enzymatic processes. The decomposition products are transported away by the metabolic system and like other metabolic waste products are eliminated from the organism. For a good compatibility of the resorbable suture material in the patient, it is important that no harmful metabolites form or are concentrated during the decomposition process. Polylactide is more particularly characterized in that during its in vivo decomposition no toxic decomposition products are formed. The further monomers in the terpolymer according to the invention, namely trimethylene carbonate (TMC) and caprolactone are also characterized by a good compatibility and the avoidance of toxic reactions.

The material according to the invention has advantageous physiological characteristics in that no plasticizer is added to the terpolymer. Its softness and flexibility result from the molecular composition and polymer structure. The softness of the terpolymer is particularly aided by a higher caprolactone and TMC content. A high lactide content aids hardness and stiffness of the polymer.

The material according to the invention can be characterized in that its degradation time in vivo is 50 to 60 days, particularly 20 to 45 days and preferably 25 to 35 days. Its resorption time in vivo can be 70 to 120 days, particularly 80 to 100 days.

During the decomposition of the material according to the invention advantageously a slightly acid medium of approximately pH 5 is obtained. This is a physiologically favourable pH-range, which also corresponds to the conditions of the human body. In particular the skin surface of the human has a pH-value of approximately 5. These pH-conditions are bactericidally and wound stimulating, which is advantageous for healing.

The material according to the invention can be characterized in that its decomposition behaviour is determined by the proportions of the monomers, particularly the lactide proportion. The degradation behaviour of the terpolymer according to the invention can be influenced and preferably adjusted by varying the lactide proportion in the polymer. Another influencing factor permitting a variation of the decomposition behaviour of the inventive polymer is the intensity and duration of gamma radiation. The treatment with gamma rays can be linked with a partial molecular weight reduction, which is expressed by reduced decomposition times. It is possible in this way to adapt the characteristics of the terpolymer according to the invention to the advantageous requirements for use. In a possible embodiment of the invention a sterilization performed with the aid of gamma rays can be simultaneously used for controlling the degradation behaviour of medical products manufactured from the terpolymer according to the invention.

The enclosed FIG. 1 shows how the degradation of the terpolymer according to the invention over time modifies its physical and mechanical characteristics. A membrane produced with DL-lactide with a thickness of 80 to 120 μm and sterilized at 37° C. and pH 7.4 and 25 kGy is decomposed in Sorensen buffer. The drawing shows the percentage decrease of the inherent viscosity, the maximum loading and the elongation at break. Within six months there is a reduction of the values to 20 to 40% of the initial values To the material according to the invention can advantageously be added one or more medically active substances. Such doped active substances can e.g. be medicaments, vaccines, antibiotics, antiseptics, growth factors, etc.

For use in a medical treatment the material according to the invention can be in the form of a single or multiple layer sheet material, in particular in film form. In one embodiment the material according to the invention can be in the form of a porous membrane. In another embodiment the material according to the invention can be in the form of a shaped article. In another embodiment the material can be in the form of a net. In yet another embodiment the material according to the invention can be in the form of a hollow membrane. In a particular embodiment the material according to the invention can be in the form of a solution. In another embodiment the material according to the invention can be in the form of a nonwoven. Such a nonwoven can in particular be produced as a melt blown nonwoven by melt blow technology. In a particular embodiment the material according to the present invention can be in the form of a composite combined with other biocompatible structures. Such composite components can be formed from resorbable and/or non resorbable materials. The composite components can be provided as textile structures. A composite can be formed according to textile and/or thermoplastic procedures.

Advantageously the material according to the invention is characterized in that it has a porous structure and in particular its porosity can exceed 85%. The pore size can be above 1 μm, particularly above 10 μm.

In a special embodiment the material according to the invention can serve as a carrier or matrix for cell cultures as a result of good proliferation characteristics.

The form in which the material according to the invention is produced depends on the intended use. For topical application to the skin of the patient are more particularly suitable fabrics such as films, sheets, nets or membranes. Liquid forms can also be advantageous for external application, such as e.g. sprayed dressings.

For use in surgery in the patient's body it is also possible to use fabrics, but advantageously also shaped articles, hollow membranes, filaments or liquid formulations, as well as coatings of implants. Examples of fabrics according to the invention are films, sheets, membranes, nonwovens, textile fabrics such as knitted and woven fabrics, etc., together with composites such as laminates.

The invention also includes a method for the manufacture of a coating material for medical treatment, particularly a wound contact material of resorbable synthetic material, characterized in that based on lactide, methylene carbonate and ε-caprolactone as monomers by polymerization a terpolymer is produced with a lactide content of maximum 85 wt. %, trimethylene carbonate in the range 5 to 20 wt. % and ε-caprolactone in the range 5 to 20 wt. % and from this is obtained a product for medical application.

In a development of the manufacturing method the terpolymer can be dissolved in a suitable solvent and produced by spreading methods into fabrics, such as sheets or membranes. Suitable solvents are e.g. ethyl acetate, acetone, chloroform, methylene chloride, carbon tetrachloride, dimethyl acetamide, formamide, tetrahydrofuran, dioxan, dimethyl sulphoxide and mixtures thereof.

In another embodiment of the manufacturing method the terpolymer can be dissolved in a suitable solvent and by phase inversion procedures constructed as a porous structure. By means of two different, intermiscible solvents, whereof one dissolves the polymer and the other does not, the polymer is precipitated in such a way that a porous membrane is left behind. Another method for producing a porous membrane can e.g. be based on lyophilization, the polymer precipitating and the frozen solvent being removed, so that in place of the solvent pores are left behind. Another way to produce a porous membrane is the sprayed web procedure. Through a suitable choice of the method conditions the pore structure and size in the membrane can be as desired.

In another procedure the terpolymer according to the invention can be thermoplastically processed by extrusion. In this way using extruders and spinnerets, it is possible to produce filaments, monofilaments or multifilaments. Such filaments can be processed by known procedures to medical products according to the invention. In addition, by extruders it is possible to produce blown, pressed or rolled films or sheets. Using extruders and the melt blow procedure it is possible to produce porous structures with a random shape. For the formation of shaped articles and free structures advantageously staple fibre technology is used.

The procedures for producing specific forms of the material according to the invention are known to the expert and are consequently not described in greater detail here.

As a function of the particular embodiment, the coating material according to the invention can be present in different thicknesses. A membrane according to the invention can have a thickness of 20 to 500 $\mu$m, particularly 50 to 250 $\mu$m, preferably 100 to 150 $\mu$m. A film according to the invention can have a thickness of 10 to 100 $\mu$m, particularly 20 to 50 $\mu$m, preferably 30 to 40 $\mu$m.

A material constructed according to the invention is advantageously suitable for use as a wound covering material in the medical treatment of humans or animals.

In a preferred embodiment it is suitable for use as a skin replacement material in the medical treatment of humans or animals.

In another embodiment it is suitable for use for adhesion prophylaxis in the medical treatment of humans or animals.

In a special embodiment it is suitable for use as a matrix for cell cultures.

In a further embodiment it is suitable for use in the coating of medical implants for the medical treatment of humans or animals.

With particular advantage the material according to the invention can be used for the medical treatment of the skin. These treatments e.g. include wound treatment, skin replacement or the protection of healthy skin against the effects of harmful environmental influences. Wound treatment covers wounds resulting from trauma, such as e.g. skin abrasions, chronic wounds, such as e.g. skin lesions in pancreatic diabetes, venous ulcers, decubital ulcers, occlusive arterial diseases and also burns.

In particular burn wounds and deep dermal wounds destroy the protective function of the skin and represent a risk for the survival of the patient. Particularly with second and third degree burn wounds and split-thickness skin taking points for transplants there is a high water loss, temperature drop, increase in germ permeability associated with an increased infection risk. The need for synthetic dressing material and/or skin substitute material arises in burns medicine, plastic surgery, as well as in the mouth, jaw and face field, including periodontology and orthodontia, in hand and plastic surgery, as well as in emergency surgery.

Different replacement strategies can be followed in skin replacement. In the case of epidermal replacement processes a skin coverage with autologous keratinocytes is preferred in conjunction with a transport matrix such as e.g. an inert polymer film of resorbable material. With dermal replacement processes a synthetic dermal matrix is made available for the infiltration and reorganization of endogenous cells. In composite skin replacement processes use is made of a combination of dermal matrix replacement with epidermal and/or dermatic cells.

Both for an optimum wound dressing and for a skin replacement there are needs with respect to a synthetic polymer material of orienting on the basis of the characteristics of human or animal skin and also for interacting physiologically with the wound bed. The terpolymer material according to the invention fulfils the aforementioned needs. It is characterized by a good adhesion to the wound bed and has a barrier function to microorganisms. It is also adequately permeable to water vapour and permits a temperature regulation via the dressing. In addition, would healing mechanisms are stimulated and local defence mechanisms assisted. The physiologically good compatible, resorbable product permits a largely inflammation-free integration in the recipient structure with controlled decomposition and remodelling of the treated body tissue. In the case of use as an external wound dressing the frequency of dressing changes can be reduced to one or two times weekly, which leads to a significant pain reduction for the patient, reduced infection risk and a significant decrease of wound trauma during which freshly epithelized cutaneous areas can be separated. In this way during skin treatment scarring can be prevented and newly formed skin with long term, good mechanical and esthetic qualities can be maintained.

The medical material of the above-described manner can also be used for the prophylaxis of adhesions during surgery in both human and veterinary medicine. As a function of the medical requirements and the desired use procedure, the material according to the invention can be used in different forms, e.g. as a membrane, solution or spray. The use of the resorbable material according to the invention can prevent undesired cicatrization of body tissue and can assist endothelialization.

Another use of the aforementioned material is the coating of medical implants introduced into the body of the patient. An example is the coating of stents with a solution of the terpolymer according to the invention. Such stents can be used for tracheal, gastrointestinal, urethral and vascular purposes.

Due to its favourable properties with respect to an infiltration of cells, the material according to the invention can also be used as a carrier or matrix for cell cultures within the framework of tissue engineering. Such a carrier/matrix can be constructed from the terpolymer according to the invention as a film, membrane, nonwoven or some other textile structure.

The resorbable material manufactured according to the invention can be prepared in per se known manner for medical use. In particular, the polymer material according to the invention can be appropriately sterilized. An appropriate sterilization process can be chosen from conventional physical or chemical methods for inactivating microorganisms or a combination of such methods. One possible sterilization method comprises gamma ray treatment. Another method for sterilizing the polymer material according to the invention for medical purposes involves the use of ethylene oxide.

Advantageously the medical material manufactured from the polymer according to the invention can be cut to an appropriate size for use and packed in an appropriate manner. Due to the hydrolytic decomposability of the terpolymer material according to the invention the medical products must be protected against moisture and high temperatures during storage, so that the strength characteristics are fully maintained up to the time of their use. Advantageously the medical products manufactured according to the invention can be dried in ready-to-use state and appropriately packed. Appropriately this can take place through a pack protecting against moisture, particularly a pack of moisture-impermeable sheet material, preferably a vacuum pack. The choice of a dry, cool storage location is also important.

Further features and details of the invention can be gathered from the following description of preferred embodiments in the form of examples. The individual features, both singly and in random combination, can be implemented together. The examples merely serve to illustrate the invention and in no way restrict the scope of the same.

EXAMPLE 1
Production of a Polymer With Lactide/caprolactone/TMC in the Ratio 75:10:15

For the production of a terpolymer 1500 g of DL-lactide, 200 g of ε-caprolactone and 300 g of trimethylene carbonate (TMC) are mixed, accompanied by stirring. Following the addition of the catalyst, 0.4 g of tin octoate (corresponding to 0.02 wt. %), heating takes place, accompanied by stirring, to 150° C. and further polymerization takes place for 24 hours at this temperature. For drawing off the reaction mixture the temperature is raised to 180 to 200° C., the polymer is discharged and after cooling is ground to a particle size of 5 mm.

EXAMPLE 2
Production of a Polymer With Lactide/caprolactone/TMC in the Ratio 80:10:10

For the production of a terpolymer 1600 g of DL-lactide, 200 g of ε-caprolactone and 200 g of TMC are mixed, accompanied by stirring. After adding the catalyst, tin octoate (0.4 g corresponding to 0.02 wt. %) heating takes place, accompanied by stirring, to 170° C. and further polymerization takes place at this temperature for 24 hours. After drawing off the reaction mixture the temperature is raised to 180 to 200° C., the polymer discharged and ground to a particle size of 5 mm after cooling.

EXAMPLE 3
Production of a Film from the Solution

In a glass reactor 240 g of granulated polymer are mixed with 800 g of ethyl acetate and an approximately 23% polymer solution is prepared, accompanied by stirring. After stirring for 4 hours the polymer solution is filtered under pressure (44 μm filter, mesh no. 325 steel wire fabric) and degasses for 12 hours. The filtered, degassed polymer solution is poured onto a glass plate and spread with a 250 μm doctor blade. The glass plate coated with the polymer solution is left for 2 hours at ambient temperature under the hood, followed by subsequent drying for 24 hours at 50° C. for reducing the residual solvent content. The thus produced films have a dry coating thickness of 20+/−5 μm, a tensile strength of >10 N/mm$^2$, a modulus of <1000 N/mm$^2$ and an elongation at break of >50%.

EXAMPLE 4
Production of a Membrane from the Solution

The production, filtration and degassing of the polymer solution are in accordance with example 3. In place of ethyl acetate, 1,4-dioxan is used as the solvent. The filtered, degassed polymer solution is poured onto a glass plate and spread using a 400 μm doctor blade. The glass plate coated with the polymer solution is immediately cooled for 2 hours at −10° C. and subsequently lyophilized under a vacuum of >0.5 mbar. The lyophilization process is ended after 12 hours. The resulting membranes have a coating thickness of 80 to 100 μm, a porosity of >85% for pore sizes of 5 to 50 μm, a tensile strength of >2 N/mm$^2$, a modulus of <1000 N/mm$^2$ and an elongation at break of >50%.

EXAMPLE 5
Production of a Nonwoven by Thermoplastic Processing 1000 g of granulated polymer according to example 1 are supplied under inert gas (argon, nitrogen) in an extruder to a spinneret and immediately prior to passing out are extruded and stretched with a very rapid air stream. The melting point and temperature of the air stream are 150 to 170° C., the blowing speed being 5 to 200 m/s. The polymer melt is then transformed by the high air flow rate into fibre-like particles and placed on a carding machine to give carding web of fine fibres. The nonwoven base can then be bonded in subsequent working steps either chemically (with solvents), thermally (using hot rolls or calenders) or mechanically (carding machine, needling machines).

What is claimed is:

1. Coating material for medical treatment, of resorbable, synthetic material, wherein it is formed from a terpolymer based on lactide, trimethylene carbonate and ε-caprolactone with a maximum lactide content of 85 wt. %, trimethylene carbonate in the range 5 to 20 wt. % and ε-caprolactone in the range 5 to 20 wt. %.

2. Material according to claim 1, wherein in the terpolymer the monomers lactide/trimethylene carbonate/ε-caprolactone are present in weight percentage ratios of 85:10:5 to 70:20:10.

3. Material according to claim 1, wherein it has a glass transition point in the range 20 to 40° C.

4. Material according to claim 3, wherein the glass transistion point is in the range 28 to 37° C.

5. Material according to claim 1, wherein in the sterilized state following treatment with gamma rays, it has a molecular weight of 50,000 to 150,000 Dalton.

6. Material according to claim 5, wherein the molecular weight is 60,000 to 90,000 Dalton.

7. Material according to claim 1, wherein in the sterilized state following treatment with gamma rays (25 kGy), it has an inherent viscosity of 0.7 to 1.2 dl/g.

8. Material according to claim 1, wherein it has an elongation of at least 50% at 37° C.

9. Material according to claim 1, wherein its degradation time in vivo is 15 to 60 days.

10. Material according to claim 9, wherein the degradation time in vivo is 20 to 45 days.

11. Material according to claim 10, wherein the degradation time in vivo is 25 to 35 days.

12. Material according to claim 1, wherein its resorption time in vivo is 70 to 120 days.

13. Material according to claim 12, wherein the resorption time in vivo is 80 to 100 days.

14. Material according to claim 1, wherein its decomposition behaviour is determined by the proportions of the monomers, with the monomer content being up to 10 wt. %.

15. Material according to claim 14, wherein the decomposition behaviour is determined by the lactide monomer proportion.

16. Material according to claim 1, wherein it contains medically active substances.

17. Material according to claim 16, wherein the active substances are medicaments.

18. Material according to claim 1, wherein it has a layered structure.

19. Material according to claim 18, wherein it is in the form of a film or sheet.

20. Material according to claim 18, wherein the layered structure comprises at least one layer of the group consisting of a porous membrane, a net, a hollow membrane and a nonwoven.

21. Material according to claim 20, wherein the nonwoven is a melt blown nonwoven.

22. Material according to claim 1, wherein it is porous.

23. Material according to claim 22, wherein its porosity is more than 85%.

24. Material according to claim 1, wherein its pore size is above 1 μm.

25. Material according to claim 24, wherein its pore size is above 10 μm.

26. Material according to claim 1, wherein it is in the form of a solution.

27. Method for the manufacture of a coating material for medical treatment, from resorbable, synthetic material, wherein on the basis of lactide, trimethylene carbonate and ε-caprolactone as monomers as a result of polymerization a terpolymer is formed with a maximum lactide content of 85 wt. %, trimethylene carbonate in the range 5 to 20 wt. % and ε-caprolactone in the range 5 to 20 wt. % and its construction as a product for medical application.

28. Method according to claim 27, wherein the terpolymer is dissolved in a solvent and constructed as fabrics by spreading methods.

29. Method according to claim 27, wherein the terpolymer is dissolved in a solvent and by phase inversion methods is formed into a porous structure.

30. Method according to claim 27, wherein the terpolymer is produced thermoplastically by extrusion to filaments or sheets.

31. Method according to claim 27, wherein the terpolymer is produced thermoplastically by melt blow technology to give porous structures.

32. Use of a coating material according to claim 1 as a wound covering material in the medical treatment of humans or animals.

33. Use of a coating material according to claim 1 as a skin replacement material in the medical treatment of humans or animals.

34. Use of a coating material according to claim 1 for adhesion prophylaxis in the medical treatment of humans or animals.

35. Use of a coating material according to claim 1 as a matrix for cell cultures.

36. Use of a coating material according to claim 1 for coating medical implants for the medical treatment of humans or animals.

* * * * *